United States Patent [19]

Hoppe et al.

[11] Patent Number: 4,839,165
[45] Date of Patent: Jun. 13, 1989

[54] COSMETIC AGENTS FOR HAIR

[75] Inventors: Udo Hoppe, Hamburg; Walter Engel, Pinneberg, both of Fed. Rep. of Germany

[73] Assignee: Beiersdorf Aktiengesellschaft, Hamburg, Fed. Rep. of Germany

[21] Appl. No.: 5,518

[22] Filed: Jan. 20, 1987

[30] Foreign Application Priority Data

Feb. 6, 1986 [DE] Fed. Rep. of Germany ....... 3603595

[51] Int. Cl.$^4$ .......................... A61K 7/06; A61K 7/08; A61K 7/11; A61K 7/13
[52] U.S. Cl. .......................................... 424/70; 8/405; 424/DIG. 1; 424/DIG. 4; 514/880; 514/881
[58] Field of Search ........................................... 424/70

[56] References Cited

FOREIGN PATENT DOCUMENTS

| | | | |
|---|---|---|---|
| 0102534 | 3/1984 | European Pat. Off. | 424/70 |
| 2828352 | 1/1980 | Fed. Rep. of Germany | 424/70 |
| 3233388 | 3/1984 | Fed. Rep. of Germany | 424/70 |
| 1337769 | 3/1962 | France | 424/73 |
| 7309660 | 7/1975 | Netherlands | 424/70 |
| 2024010 | 1/1980 | United Kingdom | 424/70 |

OTHER PUBLICATIONS

"Properties of a sericin-containing buffering shampoo", W. Engle, U. Hoppe, W. Pape, G. Sauermann, Reprint (vol. 2 Mar./Apr. 1987) from Medical Cosmetology 1, 91–110 (1987).
Copy of Application Serial No. 524,259, filed Aug. 18, 1983 "Cosmetics Containing Sericin", corresponds to Offen. 3,233,388.
Yamazaki, 1974, vol. 80, p. 19390a, Chem. Abs.
Prodenta, 1975, vol. 83, p. 33036h, Chem. Abs.
Proserpio, 1984, vol. 101, p. 157457f, Chem. Abs.
Hoppe, et al., 1984, vol. 100, p. 215305x, Chem. Abs.
Weil, 1972, vol. 76, p. 87536v, Chem. Abs.

Primary Examiner—Dale R. Ore
Attorney, Agent, or Firm—Sprung Horn Kramer & Woods

[57] ABSTRACT

Water-based cosmetic agent for hair which contains sericin and pelargonic acid as active ingredients.

8 Claims, No Drawings

COSMETIC AGENTS FOR HAIR

The invention relates to water-based cosmetic agents for hair which, in addition to customary constituents, contain sericin and pelargonic acid as active ingredients. Cosmetic agents for hair act on the hair, scalp and style. They comprise (1) Agents for cleansing and care (for example shampoos, hair waters, hair lotions, hair dressing auxiliaries, and agents for hair health), (2) Agents for improving and maintaining the style (for example hair setting lotions, hair sprays, and permanent wave agents), (3) Agents for improving the hair colour (for example hair tinting lotions, hair colorants, and lighteners).

Water-based cosmetic agents for hair containing sericin, which is a protein obtained, for example, on degumming raw silk, are already known per se from German Offenlegungsschrift 3,233,388. This describes the advantage of agents of this type as being a powerful smoothing effect on the skin and a substantive behaviour towards human hair which reduces damage to the cuticle in the surface of the hair. According to German Offenlegungsschrift 3,233,388, the cosmetic agents for hair are preferably adjusted to a neutral or acidic pH.

However, it has been established that the "alkalifree", "neutral" or "acidic" shampoos hitherto customary and available on the market have a buffer capacity which is zero or too low. That is to say, when used properly, the pH of shampoos of this type diluted to produce the suds is in the pH range of water, which is between 6.5 and 9.5 as a rule. The intended effect brought about by stabilizing the pH in the physiological range (pH 5.7 to 5.9), namely (1) a minimum of swelling of the keratinous material and (2) hence renewing and improving the attachment of the cuticular scaly layer to the hair shaft, is thus not achieved in this way. The acidic components which are customarily used are neutralized by the constituents of water and are rinsed out.

Fatty acids of medium chain length ($C_8$ to $C_{12}$), preferably decanoic acid (capric acid) or dodecanoic acid (lauric acid), have already been proposed in German Offenlegungsschrift 2,828,352 as agents for treating seborrhoeic conditions. However, solutions of effective concentrations of acids of this type have been obtained only in alcohols or in strongly alcoholic solvent mixtures.

Accordingly, the object of the invention was to develop a mild, particularly well-tolerated water-based cosmetic agent for hair which, while retaining the good skin- and hair-care properties of a sericin-containing agent, at the same time also stabilizes the pH on the scalp and the hair in the physiological range, in order to minimise as far as possible the derangement of the naural conditions on the scalp and hair when agents of this type are used. This particularly in the context of use as a supplement to therapeutic measures, for example, between recurrences of fungal or bacterial infection.

It has now been found, surprisingly, that pelargonic acid (nonanoic acid) in conjunction with sericin (possibly with the formation of a complex) can also be used as an aqueous formulation. When a water-based cosmetic agent for hair of this type is used, the pH is stabilized in the physiological range. At the same time, even on lengthy use, no scale formation is induced, on the contrary there is even a reduction in some types of dandruff.

Hence the invention relates to a water-based cosmetic agent for hair, preferably in the form of an agent for hair health, particularly preferably in the form of a shampoo, which is characterized in that, in addition to customary constituents, it contains sericin and pelargonic acid. A content of 0.01 to 1.0% by weight, preferably 0.02 to 0.6% by weight, of sericin, and 0.01 to 6.0% by weight, preferably 0.01 to 1.0% by weight, particularly preferably 0.03 to 0.5% by weight, of pelargonic acid has proved particularly suitable for this.

To achieve an optimal effect, a cosmetic agent for hair of this type is adjusted to an acidic pH (pH: 5–6) in a manner known per se by addition of a suitable acid, for example citric acid, ether carboxylic acids, alkyl ether phosphoric acids or an acidic buffer system, for example citric acid/citrate buffer.

It has been possible to demonstrate that, with a shampoo according to the invention and containing sericin and pelargonic acid, the increase in the pH is less pronounced than with a commercially available acidic shampoo without this addition, even on dilution with relatively large amounts of water, that is to say less alkalization takes place. At the concentrations normally used, this effect also operates on the hair, so that the undesired swelling of hairs and hair matrices which occurs in aqueous medium is avoided. On the other hand, without the addition of pelargonic acid swelling of the hair is already detectable.

At the same time, there is a beneficial effect on the scale status: whereas it is true that with a shampoo without pelargonic acid the scale formation decreases in the first two weeks of use, but can then increase again -in some cases even with the formation of larger scales -it is found that with a shampoo according to the invention, after the decrease in scale formation which is likewise observed, subsequently the scale status remains virtually the same.

The cosmetic agents for hair according to the invention can also contain, suited to the intended purpose of use in each case, customary components in the customary ratios of amounts in agents of this type, such as detergent substances (surfactants) of a very wide variety of type (not only anionic, cationic and non-ionic compounds but also amphoteric compounds), constituents having an emulsifying action, viscosity regulators, water-repellent substances (for example waxes, resins or silicones), stabilizers, as well as, where appropriate, pearl lustre agents, antioxidants, UV absorbers, preservatives, colorants and perfumes, plus other customary formulation constituents.

Preparation is carried out in a manner known per se, by simply mixing the constituents with stirring. In principle, the sequence of addition of the components is arbitrary, but in a preferred procedure pelargonic acid and perfume are incorporated last after the desired pH has already been set using the acid of the acidic buffer system.

The examples which follow are intended to illustrate the invention in detail, but not to restrict it to them.

Example 1
(Shampoo)

| | |
|---|---|
| Triisopropanolamine lauryl ether sulphate 40% strength | 42.0 g |

-continued

| | |
|---|---|
| Fatty acid amidoalkyl betaine 30% strength (Tego Betain L7, Goldschmidt) | 12.0 g |
| Fatty alcohol polyglycol ether carboxylic acid (Akypo RLM 150, Chem-Y-GmbH) | 2.0 g |
| Sericin | 0.4 g |
| Pelargonic acid | 0.4 g |
| Water, preservatives, perfume ad | 100 g |

The viscosity can be set as desired by addition of NaCl.

Example 2
(Shampoo)

| | |
|---|---|
| Triisopropanolamine lauryl ether sulphate 40% strength | 30.0 g |
| Fatty acid amidoalkyl betaine 30% strength | 5.0 g |
| Fatty acid amidoalkyl-dimethylamine oxide 35% strength (Aminoxid WS35, Goldschmidt) | 3.0 g |
| Fatty alcohol polyglycol ether carboxylic acid | 1.0 g |
| Coconut acid diethanolamide | 2.0 g |
| Sericin | 0.6 g |
| Pelargonic acid | 0.5 g |
| Water, preservatives, perfume ad | 100 g |

The viscosity can be set as desired by addition of NaCl.

Example 3
(Shampoo)

| | |
|---|---|
| Sodium lauryl ether sulphate 27.5% strength | 25.0 g |
| Protein-fatty acid condensate potassium salt 30% strength (Lamepon S, Grunau) | 30.0 g |
| Polypeptide solution 34% strength (Nutrilan L, Grunau) | 5.0 g |
| Alkyl polyglycol ether phosphate (Phospatal 201, Zschimmer & Schwarz) | 1.0 g |
| Sericin | 0.3 g |
| Pelargonic acid | 0.05 g |
| Water, preservatives, perfume ad | 100 g |

The viscosity can be set as desired by addition of NaCl.

Example 4
(Shampoo)

| | |
|---|---|
| Triethanolamine lauryl sulphate 48% strength | 15.0 g |
| Coco-amphoglycinate 30% strength (Dehyton G, Henkel) | 8.0 g |
| Coconut acid diethanolamide | 3.0 g |
| Alkyl polyglycol ether phosphate | 2.0 g |
| Sericin | 0.5 g |
| Pelargonic acid | 0.3 g |
| Water, preservatives, perfume ad | 100 g |

The viscosity can be set as desired by addition of NaCl.

Example 5
(Shampoo)

| | |
|---|---|
| Fatty acid amidoalkyl betaine 30% strength | 10.0 g |
| Triethanolamine lauryl sulphate 48% strength | 30.0 g |
| Coconut acid diethanolamide | 2.0 g |
| Citric acid | 1.0 g |
| Sericin | 0.3 g |
| Pelargonic acid | 0.06 g |
| Water, preservatives, perfume ad | 100 g |

The viscosity can be set as desired by addition of NaCl.

Example 6
(Pearlescent shampoo)

| | |
|---|---|
| Triisopropanolamine lauryl ether sulphate 40% strength | 40.0 g |
| Fatty acid amidoalkyl betaine 30% strength | 15.0 g |
| Fatty alcohol polyglycol ether carboxylic acid | 1.0 g |
| Coconut acid diethanolamide | 4.0 g |
| Pearl lustre agent | 4.0 g |
| Sericin | 0.4 g |
| Pelargonic acid | 0.07 g |
| Water, preservatives, perfume ad | 100 g |

The viscosity can be set as desired by addition of NaCl.

Example 7
(Pearlescent shampoo)

| | |
|---|---|
| Triisopropanolamine lauryl ether sulphate 40% strength | 42.0 g |
| Fatty acid amidoalkyl betaine 30% strength | 15.0 g |
| Coconut acid diethanolamide | 4.0 g |
| Polypeptide solution 34% strength | 2.0 g |
| Alkyl polyglycol ether phosphate | 1.0 g |
| Pearl lustre agent | 3.0 g |
| Sericin | 0.4 g |
| Pelargonic acid | 0.08 g |
| Water, preservative, perfume ad | 100 g |

The viscosity can be set as desired by addition of NaCl.

Example 8
(Pearlescent shampoo)

| | |
|---|---|
| Triisopropanolamine lauryl ether sulphate 40% strength | 45.0 g |
| Fatty alcohol polyglycol ether carboxylic acid | 2.0 g |
| Coconut acid diethanolamide | 5.0 g |
| Pearl lustre agent | 3.0 g |
| Sericin | 0.5 g |
| Pelargonic acid | 0.1 g |
| Water, preservative, perfume ad | 100 g |

The viscosity can be set as desired by addition of NaCl.

Example 9
(Pack for hair health)

| | |
|---|---|
| Cetyl/stearyl alcohol (Emulgade F, Henkel) | 8.0 g |
| Wool alcohol | 0.5 g |
| Cetyl alcohol | 0.6 g |
| Lanolin | 0.5 g |
| Laurylpyridinium chloride | 0.5 g |
| Methylpolysiloxane (Baysilon M300, Bayer) | 0.2 g |
| Sorbitol | 5.0 g |
| Citric acid | 0.5 g |
| Sericin | 0.4 g |
| Pelargonic acid | 0.1 g |
| Water, perfume, preservative ad | 100 g |

Example 10
(Emulsion for hair health)

| | |
|---|---|
| Cetyl/stearyl alcohol | 3.0 g |
| Wool alcohol | 0.5 g |
| Cetyl alcohol | 0.5 g |
| Lanolin | 0.5 g |
| Laurylpyridinium chloride | 0.5 g |
| Methylpolysiloxane | 0.2 g |
| Sorbitol | 5.0 g |
| Citric acid | 0.4 g |
| Sericin | 0.6 g |
| Pelargonic acid | 0.5 g |
| water, preservative, perfume ad | 100 g |

Example 11
(Cream rinse for hair health)

| | |
|---|---|
| Glycerol mono/distearate (Teginacid R, Goldschmidt) | 3.0 g |
| Cetyl alcohol | 0.5 g |
| Decyl oleate | 5.0 g |
| Isopropyl myristate | 2.5 g |
| Dialkyldimethylammonium chloride (Genamin DSAC, Hoechst) | 2.0 g |
| Sorbitol | 3.0 g |
| Protein hydrolysate | 2.0 g |
| Propylene glycol | 1.5 g |
| Citric acid | 0.3 g |
| Sericin | 0.3 g |
| Pelargonic acid | 0.07 g |
| Water, preservative, perfume ad | 100 g |

Example 12
(Rinse for hair health)

| | |
|---|---|
| Cetyl alcohol | 1.0 g |
| Dialkyldimethylammonium chloride | 2.0 g |
| Sorbitol | 1.0 g |
| Citric acid | 0.3 g |
| Sericin | 0.4 g |
| Pelargonic acid | 0.04 g |
| Water, preservative, perfume ad | 100 g |

We claim:

1. In a water-based cosmetic agent for hair selected from the group consisting of agents for cleansing and caring for the hair, agents for improving and maintaining hair style and agents for improving hair color, including one or more customary constituents selected from the group consisting of detergents, emulsifiers, viscosity regulators, water-repellant substances, stabilizers, pearl luster agents, antioxidants, UV absorbers, preservatives, colorants and perfumes, the improvement comprising the water-based cosmetic agent additionally containing sericin and pelargonic acid as active ingredients, said active ingredients forming a complex.

2. Cosmetic agents for hair according to claim 1, characterized by a content of 0.01 to 1.0% by weight of sericin and 0.01 to 6.0% by weight of pelargonic acid, in each case based on the total composition.

3. Cosmetic agents for hair according to claim 1, characterized by a content of 0.02 to 0.6% by weight of sericin and 0.01-1.0% by weight of pelargonic acid, in each case based on the total composition.

4. Cosmetic agents for hair according to claim 1, characterized in that they have a pH of less than 6.

5. A cosmetic agent for hair according to claim 1 in the form of a water-based shampoo containing a detergent compound selected from the group consisting of anionic surfactants, cationic surfactants, non-ionic surfactants and amphoteric surfactants, an emulsifier, an organic acid or an acidic buffer system to obtain a desired pH and, where appropriate, one or more of a customary auxiliary selected from the group consisting of antioxidants, colorants, preservatives and perfumes.

6. A cosmetic agent for hair according to claim 1 in the form of a water-based agent for hair health containing a cationic detergent, an emulsifer, a water-repellant substance selected from the group consisting of waxes, resins and silicones, an organic acid or an acidic buffer system to obtain a desired pH and, where appropriate, one or more of a customary auxiliary selected from the group consisting of antioxidants, colorants, preservatives and perfumes 7. A cosmetic agent for hair according to claim 1, characterized by a content of 0.02 to 0.6 % by weight of sericin and 0.03 to 0.5 % by weight of pelargonic acid, in each case based on the total composition.

8. A cosmetic agent for hair according to claim 1, characterized by a content of 0.01 to 1.0 % by weight of sericin and 0.03 to 0.5 % by weight of pelargonic acid, in each case based on the total composition.

* * * * *